US010034510B2

(12) United States Patent
Patel et al.

(10) Patent No.: US 10,034,510 B2
(45) Date of Patent: Jul. 31, 2018

(54) HEADGEAR FOR PROTECTIVE HEADWEAR

(71) Applicant: ILLINOIS TOOL WORKS, INC., Glenview, IL (US)

(72) Inventors: Nishank R. Patel, Appleton, WI (US); Eric T. Sommers, Appleton, WI (US); Samuel B. Petre, Wauwatosa, WI (US); John C. Mehnert, Madison, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 0 days.

(21) Appl. No.: 14/722,832

(22) Filed: May 27, 2015

(65) Prior Publication Data
US 2015/0359289 A1 Dec. 17, 2015

Related U.S. Application Data

(60) Provisional application No. 62/012,483, filed on Jun. 16, 2014.

(51) Int. Cl.
*A42B 3/08* (2006.01)
*A42B 3/14* (2006.01)
(Continued)

(52) U.S. Cl.
CPC ............... *A42B 3/085* (2013.01); *A42B 3/14* (2013.01); *A42B 3/145* (2013.01); *A42B 3/225* (2013.01); *A61F 9/06* (2013.01)

(58) Field of Classification Search
CPC ........... A42B 3/145; A42B 3/085; A42B 3/08; A42B 3/14; A42B 3/142; A42B 3/147; A61F 9/06; A42C 5/00
(Continued)

(56) References Cited

U.S. PATENT DOCUMENTS

| 1,182,367 A | 5/1916 | Gravell |
| 1,338,022 A | 4/1920 | Lamoreaux |

(Continued)

FOREIGN PATENT DOCUMENTS

| EP | 2 184 039 A1 | 5/2010 |
| EP | 2 462 825 A2 | 6/2012 |

(Continued)

OTHER PUBLICATIONS

International Search Report and Written Opinion for PCT/US2015/033054 dated Aug. 31, 2015, 12 pages.

(Continued)

*Primary Examiner* — Jameson Collier
*Assistant Examiner* — Heather Mangine
(74) *Attorney, Agent, or Firm* — Klintworth & Rozenblat IP LLP (57) ABSTRACT

In one aspect, a headgear for engaging and supporting protective headwear on a wearer's head is provided. The headgear includes a first side member positioned on a first side of the headgear, a second side member positioned on a second side of the headgear opposite the first side, a forehead strap coupled to the first and second side members and positioned on a front half of the headgear, and an occipital strap having an end coupled to one of the first side member and the second side member on the front half of the headgear and the occipital strap extending to a rear half of the headgear.

29 Claims, 6 Drawing Sheets

US 10,034,510 B2

Page 2

(51) Int. Cl.
*A42B 3/22* (2006.01)
*A61F 9/06* (2006.01)

(58) Field of Classification Search
USPC ..... 2/181, 8.2, 421, 417, 418, 419, 423, 424
See application file for complete search history.

(56) References Cited

U.S. PATENT DOCUMENTS

| | | |
|---|---|---|
| 1,601,830 A | 10/1926 | Huntsman |
| 1,994,103 A | 3/1935 | Huey |
| 2,169,745 A | 8/1939 | Shipman |
| 2,194,492 A | 3/1940 | Bowers |
| 2,411,831 A | 11/1946 | Lehmberg et al. |
| 2,487,848 A | 11/1949 | Bowers |
| 2,658,200 A | 11/1953 | Bowers, Sr. |
| 2,700,158 A | 1/1955 | Larsen |
| 2,763,006 A * | 9/1956 | Amundsen ............ A61F 9/025 2/8.1 |
| 3,074,072 A | 1/1963 | Edwards et al. |
| 3,214,768 A | 11/1965 | Bohner |
| 3,413,972 A | 12/1968 | Depping |
| 3,430,263 A | 3/1969 | Newcomb |
| 3,609,765 A | 10/1971 | Molitoris |
| 3,696,442 A | 10/1972 | Amundsen |
| 3,868,727 A | 3/1975 | Paschall |
| 3,881,478 A | 5/1975 | Rosendahl |
| 3,955,570 A | 5/1976 | Hutter, III |
| 4,040,123 A | 8/1977 | Williams |
| 4,109,320 A | 8/1978 | Anderson |
| 4,293,757 A | 10/1981 | Niemi |
| 4,335,472 A | 6/1982 | Rappleyea |
| D270,642 S | 9/1983 | Watts |
| 4,464,800 A | 8/1984 | Edwards |
| 4,479,738 A | 10/1984 | Kubnick |
| 4,499,630 A | 2/1985 | Harris |
| 4,793,001 A | 12/1988 | Accardi |
| 4,853,973 A | 8/1989 | Boochard |
| D316,020 S | 4/1991 | Fushiya |
| 5,003,632 A | 4/1991 | Claude |
| 5,012,528 A | 5/1991 | Pernicka |
| 5,040,528 A | 8/1991 | O'Neill |
| 5,044,019 A | 9/1991 | Shewchenko |
| 5,077,836 A | 1/1992 | Idoff et al. |
| D329,590 S | 9/1992 | Chapman |
| 5,386,592 A | 2/1995 | Checkeroski |
| 5,412,811 A | 5/1995 | Hildenbrand |
| D365,666 S | 12/1995 | Gumpp |
| 5,724,119 A | 3/1998 | Leight |
| D393,933 S | 4/1998 | Huh |
| 5,752,280 A | 5/1998 | Hill |
| D398,421 S | 9/1998 | Crafoord |
| D421,116 S | 2/2000 | Mattila |
| 6,032,297 A | 3/2000 | Barthold et al. |
| 6,035,451 A | 3/2000 | Burns et al. |
| 6,055,983 A | 5/2000 | Metzger |
| 6,102,033 A | 8/2000 | Baribeau |
| D433,751 S | 11/2000 | Reischel |
| 6,154,881 A | 12/2000 | Lee |
| 6,185,739 B1 | 2/2001 | Verkic et al. |
| 6,260,197 B1 | 7/2001 | Hoogewind |
| 6,264,392 B1 | 7/2001 | Wise |
| D449,103 S | 10/2001 | Legare |
| 6,298,498 B1 | 10/2001 | Burns et al. |
| 6,341,382 B1 | 1/2002 | Ryvin et al. |
| 6,367,085 B1 | 4/2002 | Berg |
| 6,393,617 B1 | 5/2002 | Paris |
| D465,568 S | 11/2002 | Petherbridge |
| D467,489 S | 12/2002 | Rubinson |
| D489,492 S | 5/2004 | Wu |
| D492,559 S | 7/2004 | Itano |
| 6,782,558 B1 | 8/2004 | Keen, Sr. et al. |
| 6,973,672 B2 | 12/2005 | Huh |
| 6,973,676 B1 | 12/2005 | Simpson |
| D520,856 S | 5/2006 | Osiecki |
| D520,859 S | 5/2006 | Osiecki |
| D521,190 S | 5/2006 | Wu |
| 7,089,603 B2 | 8/2006 | Ketterer et al. |
| D530,185 S | 10/2006 | Osiecki |
| 7,120,939 B1 * | 10/2006 | Howard ............ A42B 3/14 2/416 |
| 7,178,932 B1 | 2/2007 | Buckman |
| D543,828 S | 6/2007 | Strutin-Belinoff |
| 7,284,281 B2 | 10/2007 | Huh |
| D557,128 S | 12/2007 | Sawdon |
| 7,308,719 B2 | 12/2007 | Huh |
| 7,441,282 B2 | 10/2008 | Heine |
| D584,003 S | 12/2008 | Juhlin |
| D589,654 S | 3/2009 | Juhlin |
| D589,776 S | 4/2009 | Camp |
| D590,232 S | 4/2009 | Demers |
| 7,534,005 B1 | 5/2009 | Buckman |
| D600,094 S | 9/2009 | Hwang |
| D602,639 S | 10/2009 | Ho |
| D617,459 S | 6/2010 | Bogue |
| D626,963 S | 11/2010 | Kim |
| D632,944 S | 2/2011 | Kang |
| D635,721 S | 4/2011 | Cheng |
| 8,056,152 B2 | 11/2011 | Brace |
| D654,224 S | 2/2012 | Wu |
| D654,634 S | 2/2012 | Wu |
| 8,214,920 B1 | 7/2012 | Edgar |
| D667,173 S | 9/2012 | Juhlin et al. |
| 8,286,269 B2 | 10/2012 | Springer et al. |
| 8,336,114 B1 | 12/2012 | Lee |
| D674,150 S | 1/2013 | Juhlin et al. |
| D674,153 S | 1/2013 | Daniels et al. |
| D676,551 S | 2/2013 | Desai |
| 8,381,312 B2 | 2/2013 | Seo |
| 8,387,162 B2 | 3/2013 | Huh |
| D684,252 S | 6/2013 | Okada |
| 8,584,265 B2 | 11/2013 | Lilenthal et al. |
| 8,627,517 B2 | 1/2014 | Ahlgren et al. |
| D710,546 S | 8/2014 | Wu |
| 8,826,464 B2 | 9/2014 | Wu |
| D722,259 S | 2/2015 | Conner |
| 8,990,963 B2 | 3/2015 | Matthews |
| 9,038,198 B2 | 5/2015 | Feinberg |
| D735,949 S | 8/2015 | Dion |
| D735,951 S | 8/2015 | Birath |
| 9,125,448 B2 | 9/2015 | Klotz |
| 9,155,923 B2 | 10/2015 | Proctor |
| D742,596 S | 11/2015 | Peng |
| D743,629 S | 11/2015 | Peng |
| D747,556 S | 1/2016 | Fujita |
| D749,796 S | 2/2016 | Barmore |
| 9,427,040 B2 | 8/2016 | Leyland |
| D767,829 S * | 9/2016 | Wu ............... D29/122 |
| 9,516,911 B2 | 12/2016 | Happel |
| 9,706,805 B2 | 7/2017 | Pereira |
| 9,956,118 B2 | 5/2018 | Sernfalt |
| 2003/0135911 A1 | 7/2003 | Wang-Lee |
| 2004/0179149 A1 | 9/2004 | Wang-Lee |
| 2006/0080761 A1 | 4/2006 | Huh |
| 2006/0225187 A1 | 10/2006 | Wu |
| 2007/0113318 A1 | 5/2007 | Weston |
| 2007/0220649 A1 | 9/2007 | Huh |
| 2007/0245467 A1 | 10/2007 | Lilenthal |
| 2008/0060102 A1 | 3/2008 | Matthews |
| 2009/0089908 A1 | 4/2009 | Huh |
| 2009/0210989 A1 | 8/2009 | Becker et al. |
| 2009/0235420 A1 | 9/2009 | Chiang |
| 2010/0050325 A1 | 3/2010 | Wang-Lee |
| 2010/0212058 A1 | 8/2010 | Wanhainen |
| 2010/0229274 A1 * | 9/2010 | Ahlgren ............ A42B 3/225 2/8.2 |
| 2010/0229286 A1 | 9/2010 | Ahlgren |
| 2010/0235971 A1 | 9/2010 | Ahlgren |
| 2010/0294270 A1 | 11/2010 | Curran |
| 2011/0101890 A1 | 5/2011 | Robinson |
| 2011/0167542 A1 | 7/2011 | Bayne |
| 2011/0179541 A1 | 7/2011 | Wright |
| 2011/0219506 A1 | 9/2011 | Uttrachi |
| 2011/0265790 A1 | 11/2011 | Walker et al. |
| 2012/0144565 A1 | 6/2012 | Huh |

(56) References Cited

U.S. PATENT DOCUMENTS

| | | |
|---|---|---|
| 2012/0291172 A1 | 11/2012 | Wills |
| 2013/0111653 A1 | 5/2013 | Huh |
| 2013/0152919 A1 | 6/2013 | Billingsley et al. |
| 2014/0208476 A1 | 7/2014 | Chen |
| 2014/0298557 A1 | 10/2014 | Townsend, Jr. |
| 2015/0143618 A1* | 5/2015 | Pereira .................. A42B 1/24 2/417 |
| 2015/0143669 A1 | 5/2015 | Pereira et al. |
| 2015/0264992 A1 | 9/2015 | Happel |
| 2015/0359680 A1 | 12/2015 | Gardner |
| 2016/0081856 A1 | 3/2016 | Hofer-Kraner |
| 2016/0183622 A1 | 6/2016 | Patel |
| 2016/0360821 A1 | 12/2016 | Benton |
| 2017/0112226 A1 | 4/2017 | Watkins |

FOREIGN PATENT DOCUMENTS

| | | |
|---|---|---|
| EP | 2 462 826 A2 | 6/2012 |
| WO | 2008/025083 A1 | 3/2008 |
| WO | 2009/048829 A1 | 4/2009 |
| WO | 2009/048836 A1 | 4/2009 |
| WO | 2014160149 A2 | 10/2014 |

OTHER PUBLICATIONS

International Search Report and Written Opinion for PCT/US2015/035714 dated Oct. 8, 2015, 11 pages.
Miller 9400i welding helmet with an integrated grind shield, published at least as early as Jun. 16, 2014, 1 page.
Speedglas 9100FX welding helmet with an integrated grind shield, published at least as early as Jun. 16, 2014, 1 page.
Speedglas 9002X Flexview welding helmet with an integrated grind shield, published at least as early as Jun. 16, 2014, 1 page.
Miller 9400i PAPR welding helmet with powered air purifying system, belt mounted blower with breathing tube connecting to manifold inside head assembly, published at least as early as Jun. 16, 2014, 1 page.
Speedglas 9100X Air Adflo welding helmet with airflow delivery mechanism, published at least as early as Jun. 16, 2014, 1 page.
Speedglas 9100FX Air Adflo welding helmet with airflow delivery mechanism, published at least as early as Jun. 16, 2014, 1 page.
Miller headgear for a welding helmet, published at least as early as Jun. 16, 2014, 1 page.
Speedglas headgear for a welding helmet, published at least as early as Jun. 16, 2014, 1 page.
International Search Report and Written Opinion for PCT/US2015/035713 dated Oct. 27, 2015, 17 pages.
nyopools.com, How to set up the zodiac T5 suction cleaner through your skimmer, https://webarchive.org/web/20130627095500/http://www.inyopools.com/HowToPage/How-to-set-up-the-zodiac0t5-cleaner-through-your-skimmer.aspx, Jun. 27, 2013, Retreived via Wayback Machine on Apr. 19, 2016.
International Search Report and Written Opinion for PCT/US2015/065213 dated Mar. 16, 2016, 13 pages.

* cited by examiner

HEADGEAR FOR PROTECTIVE HEADWEAR

RELATED APPLICATIONS

The present application claims the priority benefit of U.S. Provisional Patent Application Ser. No. 62/012,483, filed Jun. 16, 2014, the content of which is incorporated by reference herein.

FIELD OF THE INVENTION

The present disclosure generally relates to protective headwear and, more particularly, to headgear within protective headwear.

BACKGROUND

Protective headwear typically includes headgear within the headwear to engage a wearer's head and support the protective headwear upon the wearer's head. Conventional headgear is uncomfortable, unstable on a wearer's head, and poor at accommodating different size heads.

SUMMARY

Thus, a need exists for headgear that resolves one or more of these deficiencies.

In one aspect, it is desirable to have headgear that is comfortable, stable, and capable of adequately accommodating heads of varying size.

In one aspect, a headgear for protective headwear is provided and includes a pivotal forehead strap.

In one aspect, a headgear for protective headwear is provided and includes a forehead strap including a first member, a second member space-apart from the first member and a cavity between the first member and the second member.

In one aspect, a headgear for protective headwear is provided and includes an occipital strap including two ends with one end on each side of the headgear and the two ends positioned on a front half of the headgear, wherein the occipital strap is pivotable about the two ends.

In one aspect, a headgear for engaging and supporting protective headwear on a wearer's head is provided. The headgear includes a first side member positioned on a first side of the headgear, a second side member positioned on a second side of the headgear opposite the first side, a forehead strap coupled to the first and second side members and positioned on a front half of the headgear, and an occipital strap having an end coupled to one of the first side member and the second side member on the front half of the headgear and the occipital strap extending to a rear half of the headgear.

In one aspect, the occipital strap may be pivotally coupled to the one of the first and second side members at the end of the occipital strap.

In one aspect, the forehead strap may be pivotally coupled to the first and second side members. The occipital strap and the forehead strap may be pivotally coupled to the one of the first and second side members at a same location.

In one aspect, the forehead strap may be pivotally coupled to the first and second side members. The forehead strap and the occipital strap may pivot about a same pivot axis.

In one aspect, the headgear may further include a tightening member. The occipital strap may be engaged by the tightening member on the rear half of the headgear.

In one aspect, the occipital strap may include a body having an arcuate shape along at least a portion of the body.

In one aspect, the occipital strap may include a body having a complex shape comprised of at least one linear portion and at least one arcuate portion.

In one aspect, the body of the occipital strap may have a first linear portion, a first arcuate portion, a second linear portion and a second arcuate portion.

In one aspect, a headgear for engaging and supporting a protective shell on a wearer's head is provided. The protective shell is rotatable relative to the headgear about a shell axis. The headgear includes a first side member positioned on a first side of the headgear, a second side member positioned on a second side of the headgear opposite the first side, a forehead strap coupled to the first and second side members and positioned on a front side of the shell axis, and an occipital strap having an end coupled to one of the first side member and the second side member on the front side of the shell axis and the occipital strap extending to a rear side of the shell axis opposite the front side.

In one aspect, the occipital strap may be pivotally coupled to the one of the first and second side members at the end of the occipital strap.

In one aspect, the forehead strap may be pivotally coupled to the first and second side members. The occipital strap and the forehead strap may be pivotally coupled to the one of the first and second side members at a same location.

In one aspect, the forehead strap may be pivotally coupled to the first and second side members. The forehead strap and the occipital strap may pivot about a same pivot axis.

In one aspect, the pivot axis may be positioned above the shell axis.

In one aspect, the headgear may further include a tightening member. The occipital strap may engage the tightening member on the rear side of the headgear.

In one aspect, a protective headwear is provided and includes a shell, a shield coupled to the shell and configured to allow at least partial viewing there through by a wearer of the protective headwear, and a headgear pivotally coupled to the shell. The headgear is configured to engage a wearer's head to support the shell relative to the wearer's head and facilitate pivoting of the shell about a shell axis relative to the headgear between a downward position and an upward position. The headgear includes a first side member on a first side of the headgear, a second side member on a second side of the headgear opposite the first side, and a forehead strap coupled to and extending between the first and second side members on a front side of the shell axis. The forehead strap is configured to engage a wearer's forehead with the headgear worn by a wearer. The headgear also includes an occipital strap having an end coupled to one of the first member and the second member on the front side of the shell axis and extending to a rear side of the shell axis opposite the front side.

In one aspect, the occipital strap may be pivotally coupled to the one of the first and second side members at the end of the occipital strap.

In one aspect, the forehead strap may be pivotally coupled to the first and second side members. The occipital strap and the forehead strap may be pivotally coupled to the one of the first and second side members at a same location.

In one aspect, the forehead strap may be pivotally coupled to the first and second side members. The forehead strap and the occipital strap may pivot about a same pivot axis.

In one aspect, the pivot axis may be positioned above the shell axis.

In one aspect, the headgear may further include a tightening member. The occipital strap may be engaged by the tightening member on the rear side of the headgear.

In one aspect, the protective headwear may be a welding helmet and the shield may be a welding shield.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
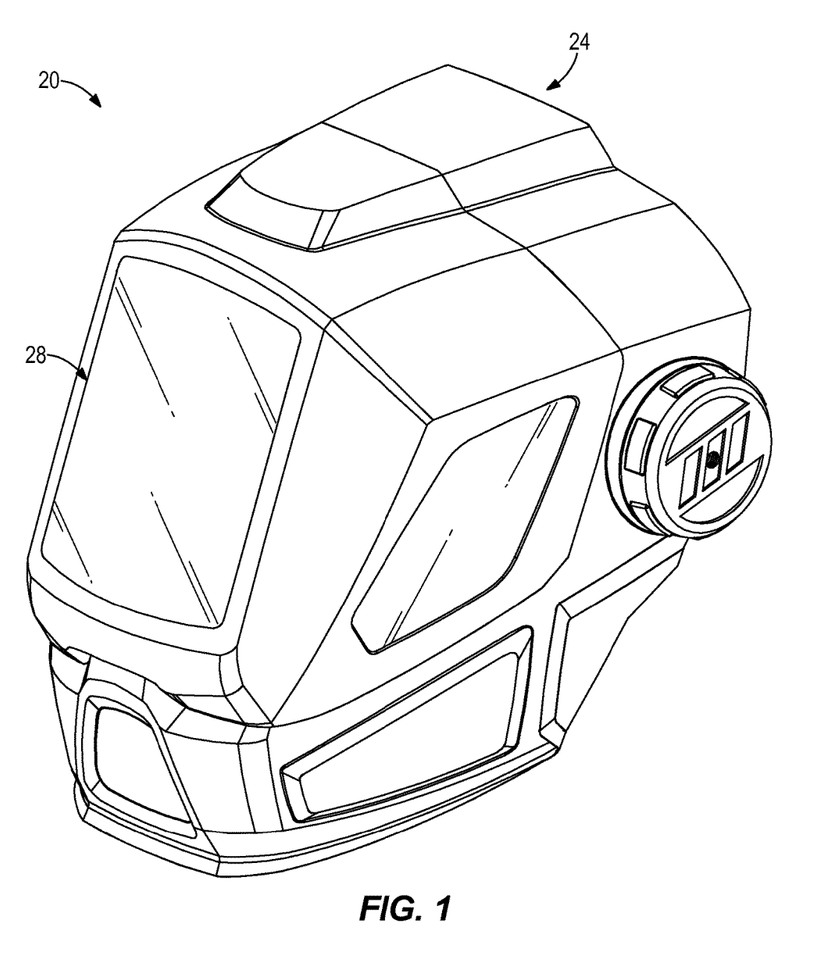
FIG. 1 is a top, front perspective view of one example of a protective headwear, according to one aspect of the present disclosure.

Referring to FIG. 1, one example of protective headwear 20 is illustrated. In this illustrated example, the protective headwear 20 is a welding helmet. The welding helmet 20 includes an outer shell 24, a first shield 28, a second shield (beneath the first shield 28 and not shown in the figures), and headgear 36 (see FIG. 2) positioned within the outer shell 24. The first shield 28 may be a welding shield and is coupled to the outer shell 24 over the second shield. The first shield 28 is tinted or otherwise darkened in order to inhibit damage to a wearer's eyes while performing a welding process. The second shield is coupled to the outer shell 24 beneath the first shield 28 and is less tinted or more transparent than the first shield 28. In one example, the second shield has no tinting or darkening and is completely transparent. The second shield may be referred to as a grinding shield.

Figure 2:
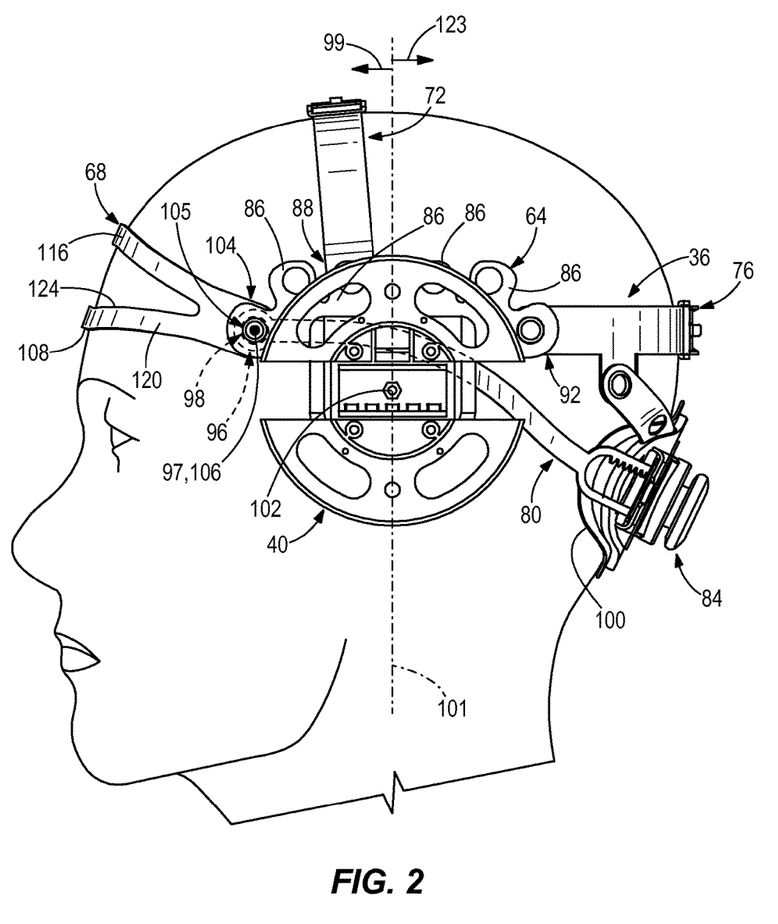
FIG. 2 is a side view of one example of a portion of headgear that may be included in the protective headwear shown in FIG. 1, according to one aspect of the present disclosure.
Figure 3:
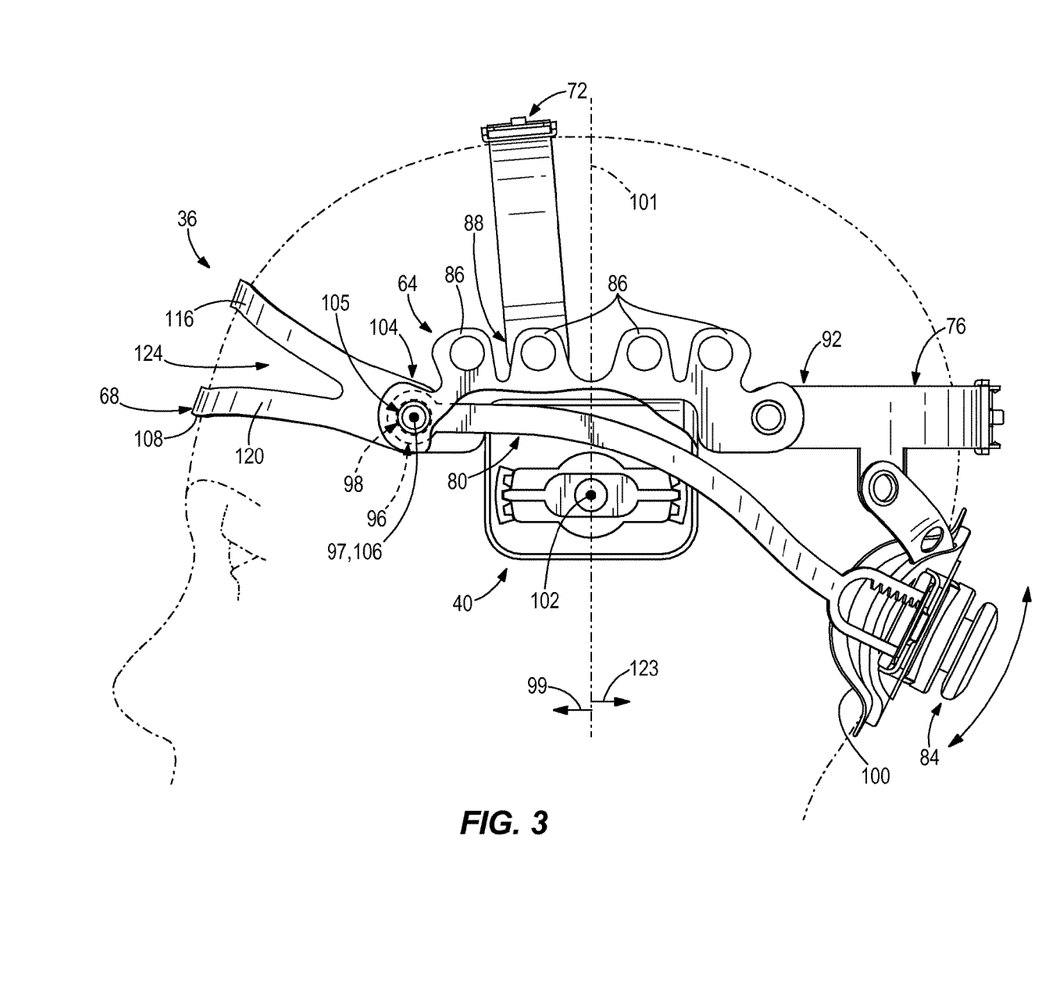
FIG. 3 is a side view of a portion of the headgear shown in FIG. 2, according to one aspect of the present disclosure.

Referring now to FIGS. 2-7, one example of headgear 36 is illustrated. One side of the headgear 36 is illustrated in FIG. 2, but it should be understood that the headgear 36 may be a substantial mirror image about a vertical plane extending through a center of the headgear 36 from front to rear (and a wearer's head when the headgear 36 is worn). In other words, the headgear 36 is symmetrical on both sides of a wearer's head. The headgear 36 is capable of coupling to and being part of the exemplary protective headwear 20 illustrated in FIG. 1 or the headgear 36 may be coupled to and be part of other types of protective headwear 20. For example, the headgear 36 may be coupled to hard hats, bicycle helmets, or any other type of headwear capable of providing protection to a wearer's head. The headgear 36 is capable of engaging a wearer's head and supporting the protective headwear 20 on the wearer's head. The headgear 36 may be coupled to the outer shell 24 of the protective headwear 20 in a variety of manners such as, for example, movably coupled, pivotally coupled, rigidly coupled, unitarily formed as one-piece with, among other manners.

With particular reference to FIG. 2, the headgear 36 includes a coupling member 40 on each side of the headgear 36 for coupling to the outer shell 24 on both sides of the outer shell 24. Each coupling member 40 allows for selective coupling of the outer shell 24 to the headgear 36 in a plurality of positions. The outer shell 24 is coupled to the headgear 36 in one position at a time on each side and remains rigidly coupled to the headgear 36 in that position until the outer shell 24 is actively decoupled from the headgear 36. The various mounting positions provide a wearer with the ability to adjust the outer shell 24 relative to the wearer's head.

In another example, an outer shell may be coupled to headgear in another manner. In this example, the outer shell may include a track or path defined in both sides thereof and the headgear may include a coupling member on each side thereof to cooperate with the respective track. Each coupling member may include a projection positioned within and slidable along the respective track. A securing member may be coupled to each coupling member and may be selectively engaged and disengaged to lock or secure the coupling members relative to the outer shell. In this example, each securing member may include a threaded member that may be turned in a first direction to tighten or secure the respective coupling member to the outer shell and inhibit movement of the headgear relative to the outer shell, and turned in a second direction to loosen or unsecure the respective coupling member from the outer shell to allow movement of the coupling member relative to the outer shell. This movement allows the wearer to adjust the outer shell relative to the wearer's head as desired. In this example, the coupling member and headgear translate or slide relative to the outer shell. In other examples, the tracks and coupling members may have different shapes, and the coupling members and the headgear may move in different manners than the illustrated translation. For example, the tracks may have arcuate shapes, at least in part, and the coupling members and the headgear 36 may move along an arcuate path relative to the outer shell. It should be understood that the headgear may be moveable relative to the outer shell in any desired manner and all of such possibilities are intended to be within the spirit and scope of the present disclosure. It should also be understood that the headgear may be coupled, locked or secured to the outer shell in any desired manner and all of such possibilities are intended to be within the spirit and scope of the present disclosure.

In another example, an outer shell may be coupled to headgear in another manner. In this example, the headgear allows pivot action between the outer shell and headgear. The headgear has laterally extending arms with a non-pivoting end. The non-pivoting end is coupled to a component which has a track that allows the non-pivoting end of the headgear arms to slide forward and backwards within that track. This allows the user to adjust a distance of the outer shell relative to their face. The component does not rotate and is fixed to the headgear with one degree of freedom allowing the components to slide forwards and backwards. The component is coupled to a second component. The second component is then coupled to the outer shell. The outer shell rotates with respect to the headgear as the second component pivots on the component. This pivot action is guided by posts that rotate within slotted holes. A bushing is coupled to the second component and placed between the component and the second component to reduce the frictional wear as the two components rotate about each other. A third component has a threaded hub through which a screw from the component threads. The third component can be rotated to adjust compressive forces for the pivot mechanism components sandwiched between the first and third components. This allows the user to control the frictional resistance of the pivot mechanism allowing control over angular velocity of the outer shell as it rotates about the headgear. The second component has a multitude of holes allowing fins protruding from the outer shell to slide into these holes locking the second component and the outer shell together preventing them from rotating about one another. The angle at which the second component is coupled to the outer shell is controlled by which the holes and the fins are slid into. This controls the tilt angle of the outer shell relative to the user's face. A fourth component is a snap-on piece that is non-rotatably coupled to the end of a threaded screw. As the first component remains fixed relative to the outer shell and the second component, the coupling of the fourth component to the first component allows it to also remain fixed. So as the third component is rotated to adjust the friction resistance, the fourth component will remain stationary relative to it.

Referring again to FIGS. 2-7, the headgear 36 also includes a side member 64 on each side of the headgear 36, a forehead strap 68, a top strap 72, a rear strap 76, an occipital strap 80 on each side of headgear 36 and a tightening member 84 coupled to the occipital straps 80. The top strap 72 is pivotally coupled at its ends 88 to respective side members 64 and is positioned to extend over a crown or top of a wearer's head. Each side member 64 includes a plurality of coupling locations 86 to which the ends 88 of the top strap 72 may be selectively pivotally coupled. In the illustrated example, the side members 64 each include four coupling locations 86. Alternatively, the side members 64 may include any number of coupling locations 86 and all of such possibilities are intended to be within the spirit and scope of the present disclosure.

Protective headwear 20 is commonly used in non-level orientations such as, for example, a downward angle (e.g., during welding, the welder is looking downward and forward toward the welding area), an upward angle (e.g., a wearer may be looking upward and overhead), etc. In such non-level orientations, the top strap 72 minimizes shifting of the protective headwear 20 relative to the wearer's head as a result of the top strap 72 extending over the crown or top of the wearer's head. The rear strap 76 is pivotally coupled at its ends 92 to respective side members 64 and is positioned to extend around a rear of a wearer's head. In the illustrated example, the top strap 72 and the rear strap 76 are oriented in a perpendicular manner relative to each other. In other examples, the top strap 72 and the rear strap 76 may be oriented in other manners relative to each other. The ends 88, 92 of the top and rear straps 72, 76, and their associated pivots or pivot points, are located in close proximity to each other on the side members 64, which may also minimize shifting of the protective headwear 20. In other examples, one or both of the top and rear straps 72, 76 may be rigidly and non-pivotally coupled to the side members 64.

In the illustrated example, the headgear 36 may be considered to include a single occipital strap 80 with two portions, one portion on each side of the headgear that are coupled together at a rear of the headgear 36 by the tightening member 84, or the headgear 36 may be considered to include two occipital straps 80, one occipital strap 80 on each side of the headgear and coupled together at a rear of the headgear by the tightening member 84. For purposes of the following description, which is not intended to be limiting one way or the other, but rather to demonstrate principles of the present disclosure, this example will reference two occipital straps 80 with one occipital strap 80 on each side of the headgear 36.

In one example, the occipital straps 80 are pivotally connected at ends 96 to respective side members 64, are positioned under the side members 64 (i.e., between the side members 64 and a wearer's head), extend rearward and downward relative to the side members 64, drop down below the rear strap 76, wrap around or extend along the occipital crest of a wearer, then extend under the occipital crest. The occipital straps 80 have a height or thickness that is smaller than a height or thickness of the top and rear straps 72, 76. The position of the occipital straps 80 allow pressure originating from the protective headwear 20 to be applied to bony structure (e.g., the occipital bone and crest of a skull) of the wearer's head where the wearer has less of a perception of pressure than on soft tissue of the wearer's head.

In the illustrated example, the occipital straps 80 are compliant to the wearer's head. The occipital straps 80 may be made of a variety of different materials and have a variety of shapes, as long as the occipital strap 80 is compliant.

In one example, pivots 98 where the occipital straps 80 pivotally couple at ends 96 to the side members 64 are positioned on a front half 99 of the headgear 36 or protective headwear 20. That is, if a vertical plane 101 was oriented through a center of the headgear 36 or a wearer's head when wearing the protective headwear 20 and extended from one side member 64 to the other side member 64 or from a wearer's ear to ear (rather than front to rear), the pivots 98 would be positioned to a front or front side of such a vertical plane 101. In other words, the pivots 98 would be positioned between the vertical plane 101 and a forward most part of the forehead strap 68. The pivots 98 define a pivot axis 97 about which each end of the occipital straps 80 pivots.

In one example, the pivots 98 of the occipital straps 80 are positioned in front of a pivot axis or shell axis 102 about which the outer shell 24 rotates relative to the headgear 36. In this example, the pivots 98 are located between the pivot axis 102 and a forward most part of the forehead strap 68.

In one example, the pivots 98 of the occipital straps 80 are positioned in front of and above the pivot axis 102 of the outer shell 24. In this example, the pivots 98 are located between the pivot axis 102 of the outer shell 24 and a forward most part of the forehead strap 68, and are between the pivot axis 102 of the outer shell 24 and an upper most part of the top strap 72.

Figure 7:
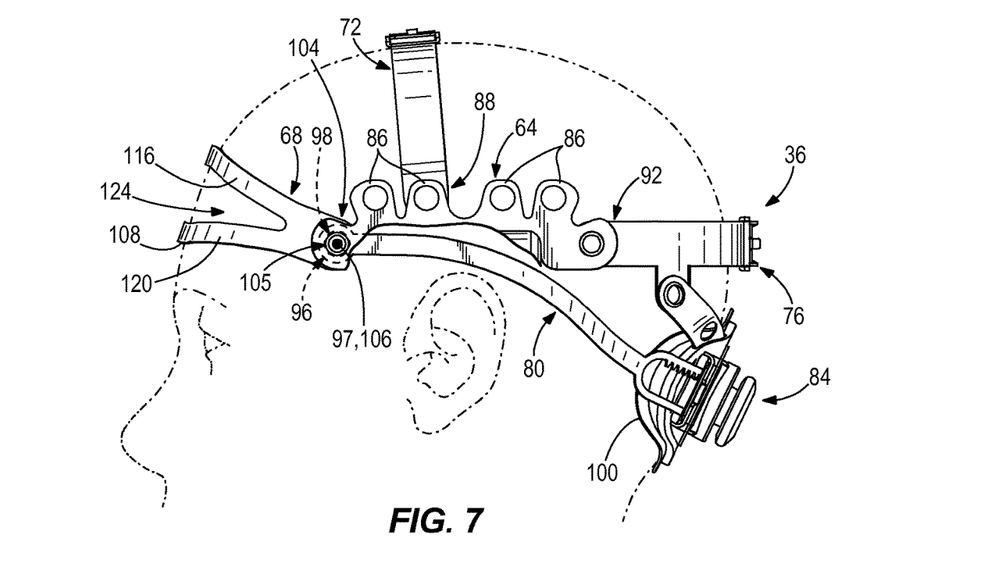
FIG. 7 is a side view of a portion of the headgear shown in FIG. 2, according to one aspect of the present disclosure.

In one example, the pivots 98 may be located above and forward of a wearer's ears (see FIG. 7). In one example, the pivots 98 are positioned adjacent or on a wearer's forehead.

Figure 4:
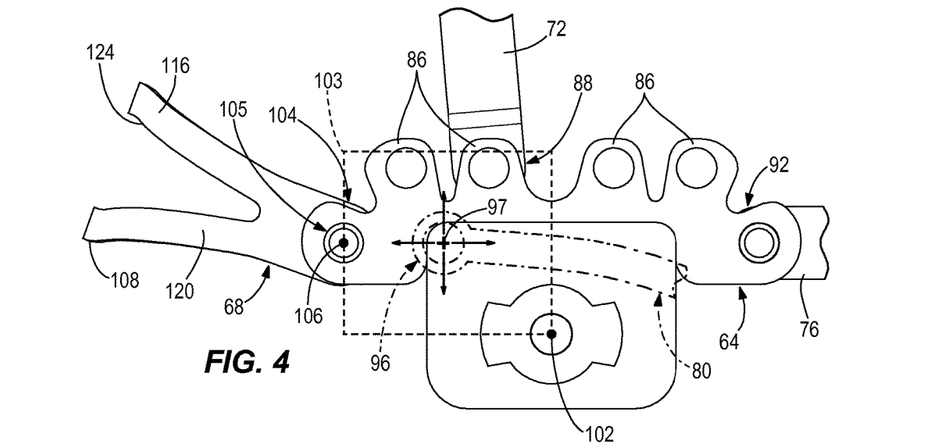
FIG. 4 is a side view of a portion of the headgear shown in FIG. 2 illustrating one example of an area that may be occupied by a pivot of an occipital strap, according to one aspect of the present disclosure.
Figure 5:
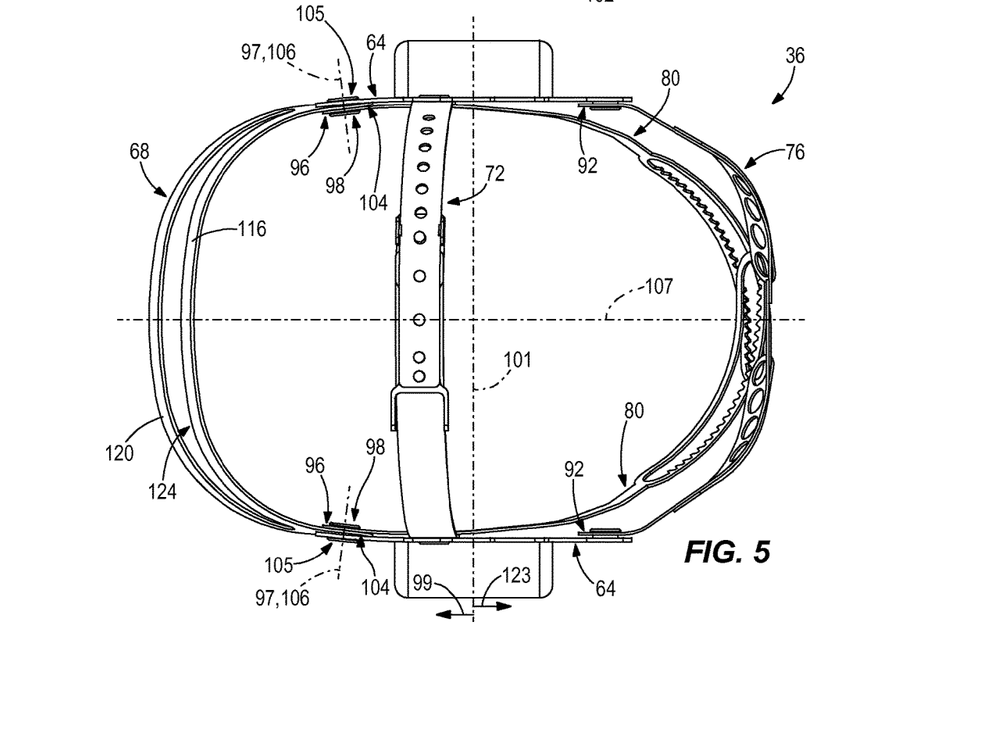
FIG. 5 is a top view of a portion of the headgear shown in FIG. 2, according to one aspect of the present disclosure.
Figure 6:
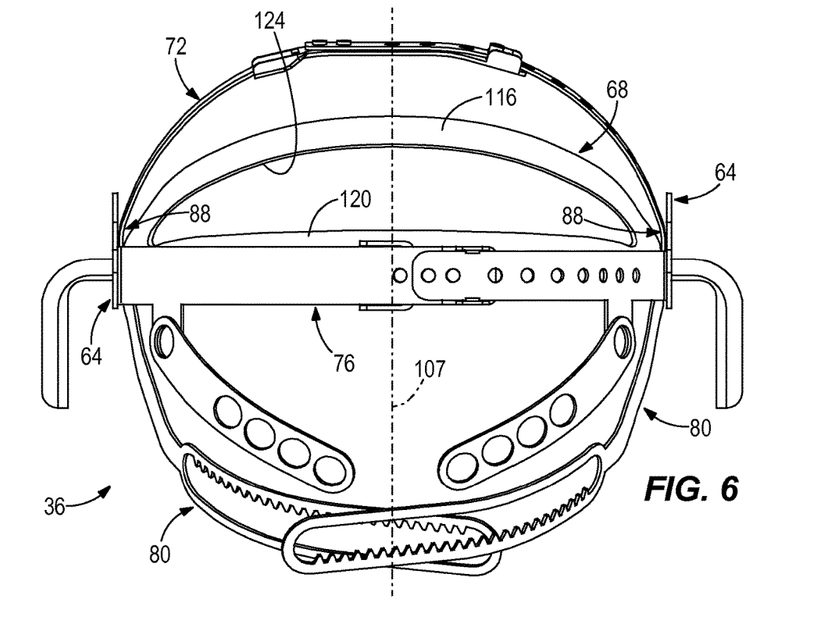
FIG. 6 is a rear view of a portion of the headgear shown in FIG. 2, according to one aspect of the present disclosure.

With reference to FIG. 4, one example of a possible area that may be occupied by the pivots 98 and pivot axis 97 is illustrated. In this example, a dashed box 103 represents one example of an area that may be occupied by the pivots 98 and the pivot axis 97. This exemplary area is between the pivot axis 102 of the outer shell 24 and pivots 105 of the forehead strap 68, and above the pivot axis 102 of the outer shell 24. This dashed box 103 is intended to demonstrate that the pivots 98 of the occipital straps 80 may be positioned in a wide variety of locations, not all of which may necessarily be explicitly mentioned herein, but all of which are intended to be within the spirit and scope of the present disclosure.

The pivots 105 of the forehead strap 68 define a pivot axis 106 at each end 104 of the forehead strap 68.

In one example and with reference to FIGS. 2, 3 and 5-7, the pivots 98 of the occipital straps 80 may be at the same position as the pivots 105 of the forehead strap 68. That is, the forehead strap 68 and the occipital straps 80 may be coupled to the side members 64 at the same position and pivot relative to the side members 64 about the same pivot axis. In this example, the pivot axes 97, 106 may be the same pivot axis or they may be co-linear.

The high and forward pivots 98 of the occipital straps 80 may allow for a greater range of motion in the occipital straps 80 (see, e.g., FIG. 3) and direct pressure or force to the forehead strap 68.

The headgear 36 further includes a pad 100 coupled to the occipital straps 80 and positioned at a rear of the headgear 36. The pad 100 is capable of engaging a rear of the wearer's head to provide comfort and further support. When the tightening member 84 is tightened by pulling the occipital straps 80 and causing the occipital straps 80 to overlap to a greater extent at a rear of the headgear 36 (see FIGS. 5 and 6), the pad 100 rises up and under the occipital crest of the wearer's head to secure the headgear 36 in place using the natural geometry of the wearer's head.

Figure 8:
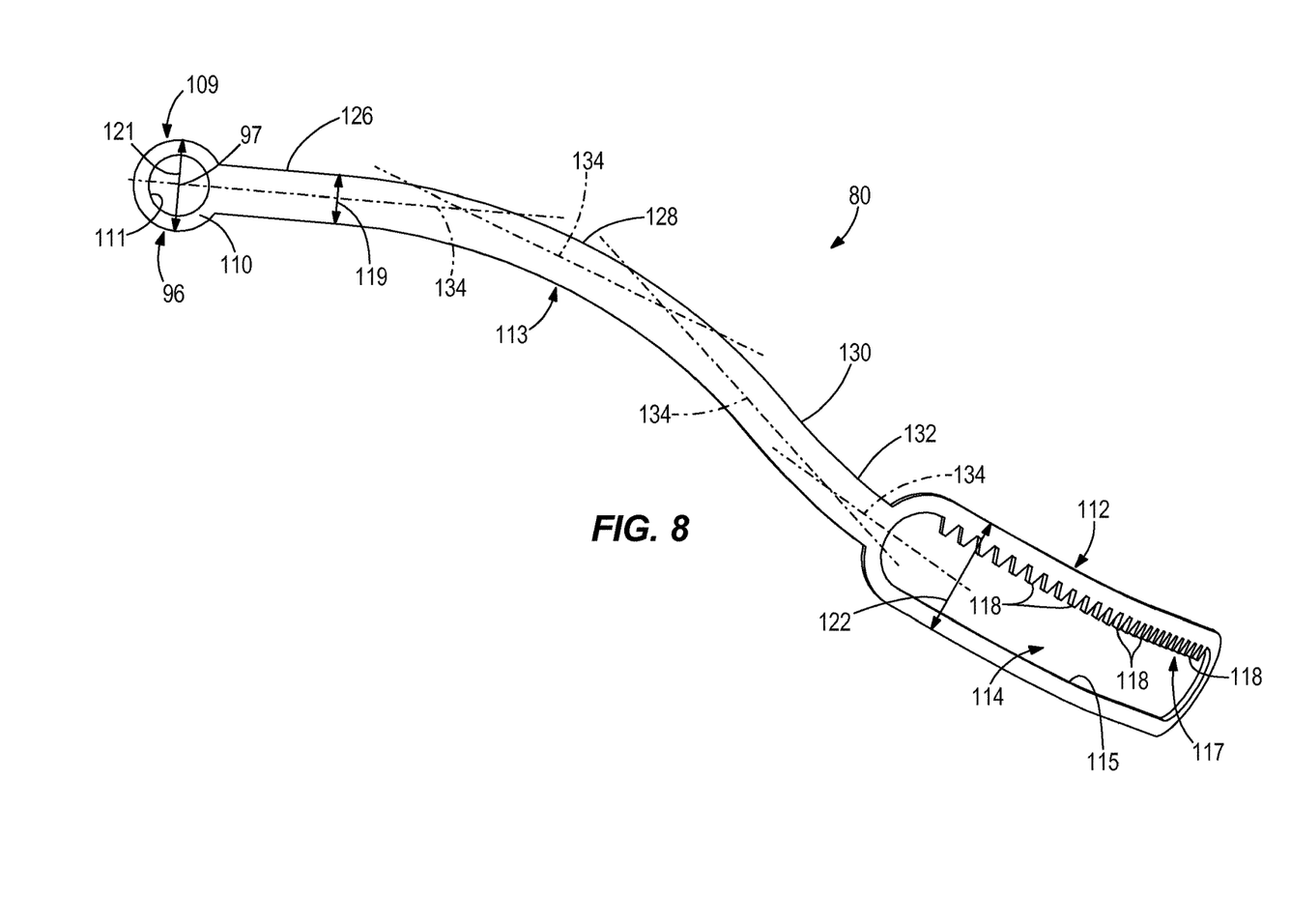
FIG. 8 is a side view of one example of an occipital strap of the headgear shown in FIG. 2, according to one aspect of the present disclosure.

Referring now to FIG. 8, one example of one of the occipital straps 80 is shown. As indicated above, an occipital strap 80 is positioned on each side of the headgear 36 and such occipital straps 80 are substantial mirror images of each other relative to a vertical plane 107 extending through a middle or center of the headgear from a front of the headgear 36 to a rear of the headgear 36. Thus, only a single occipital strap 80 will be addressed in greater detail herein with it being understood that this description of the occipital strap 80 also applies to the other occipital strap 80. The illustrated example of an occipital strap 80 is not intended to be limiting upon the present disclosure. Rather, the occipital straps 80 may have a wide variety of shapes and sizes, and all of such possibilities are intended to be within the spirit and scope of the present disclosure.

In this illustrated example, the occipital strap 80 includes a coupling 109 comprised of a hub 110 and an aperture 111 extending through the hub 110. The coupling 109 provides the location for pivots 98 to pivotally couple the occipital strap 80 to the respective side member 64 and provides the pivot axis 97 about which the occipital strap 80 pivots. The occipital strap 80 also includes an adjustment portion 112 and a body 113 extending between the coupling 109 and the adjustment portion 112. In the illustrated example, the adjustment portion 112 defines an adjustment aperture 114 therein including a flat or smooth side 115 and a jagged or saw-tooth side 117. The jagged side 117 of the adjustment aperture 114 includes a plurality of projections 118 engageable by the tightening member 84 to facilitate adjustment of the occipital strap 80. The adjustment aperture 114 may include any number of projections 118 and any size of projections 118. In the illustrated example, the body 113 has a first height or thickness 119, which is smaller or less than heights or thicknesses 121, 122 of both the coupling 109 and the adjustment portion 112.

In one example, the body 113 of the occipital strap 80 is at least partially arcuate. In one example, the body 113 of the occipital strap 80 is at least partially straight or linear and at least partially arcuate. In one example, the occipital strap 80 includes an arcuate portion and a straight or linear portion. In one example, the body 113 has a complex shape. As used herein, an object having a complex shape may refer to the object changing shape at least once. For example, the body 113 of the occipital strap 80 may have a complex shape if the body changes from being linear to being arcuate. In one example and with reference to the illustrated example, the body 113 has a complex shape and includes a first straight or linear portion 126, a first curved or arcuate portion 128, a second straight or linear portion 130 and a second curved or arcuate portion 132. Intersections of dashed lines 134 illustrated in FIG. 8 represent changes in shape. In the illustrated example, the body 113 of the occipital strap 80 changes shape three times. For example, the body 113 changes from: 1) the first linear portion 126 to the first arcuate portion 128; 2) the first arcuate portion 128 to the second linear portion 130; and 3) the second linear portion 130 to the second arcuate portion 132. The shape of the occipital strap 80 is important to position the occipital strap 80 so it does not interfere with a wearer's ear no matter the position to which the occipital strap 80 is pivoted and to apply force to desired locations on a wearer's head (as described above). The illustrated example and other possible examples of the occipital straps 80 accomplish this feat.

In one example, the occipital straps 80 extend from a position in a front half 99 of the headgear 36 or protective headwear 20 to a position in a rear half 123 of the headgear 36 or protective headwear 20. In one example, the occipital straps 80 extend from a position in front of the shell axis 102 about which the outer shell 24 rotates relative to the headgear 36 to a position rearward of the shell axis 102 about which the outer shell 24 rotates relative to the headgear 36. In one example, the occipital straps 80 extend from pivots 105 about which the forehead strap 68 rotates to a position rearward of the shell axis 102 about which the outer shell 24 rotates relative to the headgear 36. In one example, the occipital straps 80 extend from a position above the shell axis 102 to a position below the shell axis 102. In one example, the occipital straps 80 extend from a position in front of and above the shell axis 102 to a position rearward of and below the shell axis 102.

With continued reference to FIGS. 2-7, the forehead strap 68 is pivotally coupled to the remainder of the headgear 36 at the pivots 105. In other examples, the forehead strap 68 may be rigidly and non-pivotally coupled to the side members 64. In such examples, the forehead strap 68 may be bonded, fastened, unitarily formed as one-piece, adhered, or rigidly and non-pivotally coupled to the side members in any other manner.

Returning to the illustrated example, the forehead strap 68 includes two ends 104 with both ends 104 pivotally coupled to respective side members 64 adjacent the wearer's forehead. Human heads have a variety of forehead slopes and the pivoting forehead strap 68 accommodates such varying forehead slopes. As a wearer begins to place the headgear 36 on his/her head, the wearer will pull the headgear 36 down onto his/her head, the forehead strap 68 will slide down the wearer's forehead, and will terminate sliding down the wearer's head at an appropriate point on the wearer's forehead based on the slope of the wearer's forehead. It is likely that the remainder of the headgear 36 is not completely down and supported upon the wearer's head when the forehead strap 68 is in this position. The pivoting ends 104 or pivots 105 of the forehead strap 68 allow the remainder of the headgear 36 to continue to move downward until the top strap 72 engages the crown of the head and the headgear 36 is supported on the wearer's head. The pivoting forehead strap 68 will lie flat or substantially flat against a wearer's forward and evenly distribute pressure to the wearer's forehead, rather than apply a significant quantity of pressure at a single point or edge.

In the illustrated example, the pivots 105 of the forehead strap 68 are at the same positions as pivots 98 of the occipital straps 80, thereby causing the forehead strap 68 and the occipital straps 80 to pivot relative to the side members 64 about the same pivot axis. In other words, the pivot axis 106 of the forehead strap 68 and the pivot axis 97 of the occipital straps 80 are co-linear or substantially co-linear.

As can be seen in FIG. 2, a longitudinal extent of the forehead strap 68 is not aligned, co-linear or co-planar with a longitudinal extent of the side members 64 and the rear strap 76, and is instead angled or transverse slightly upward to match a forehead slope of a wearer. In this example, the wearer's head has a forehead slope that prevents the forehead strap 68 from aligning with the side members 64 and the rear strap 76. In conventional headgear, the forehead strap is not pivotal and is aligned with the rear strap. In some instances of conventional headgear, the forehead strap and the rear strap are the same, unitary strap. With such a conventional design, the conventional forehead strap would have prevented the headgear from settling completely onto a wearer's head and/or a front bottom edge of the conventional forehead strap would dig into the wearer's forehead. The pivotal forehead strap 68 of the present disclosure allows the headgear 36 to settle completely and properly on a wearer's head and inhibits a front lower edge 108 of the forehead strap 68 from digging into the wearer's head.

In some examples, the pivoting forehead strap 68 may eliminate the need to include a tightening member that provides additional pressure to secure the headgear 36 to a wearer's head. In some examples, the forehead strap 68 may also include padding or other soft material on at least an interior surface thereof (and, alternatively, wrapped around the forehead strap 68) configured to engage a wearer's forehead and provide additional comfort. The pivoting forehead strap 68 also provides a self-adjusting feature that allows a wearer to adjust or move the protective headwear 20 and headgear 36 relative to their head and the pivoting forehead strap 68 accommodates that movement to resettle the headgear 36 and the protective headwear 20 on the wearer's head.

With continued reference to FIGS. 2-7, the forehead strap 68 is a split forehead strap 68 including an upper member 116, a lower member 120 and a space or cavity 124 between the upper member 116 and the lower member 120. The split forehead strap 68 distributes pressure or force applied to a wearer's forehead by the protective headwear 20 over a larger surface area, while also having minimal contact area with the wearer's forehead as a result of the cavity 124. Additionally, air can access a wearer's forehead through the cavity 124, thereby increasing the comfort of a wearer while wearing the protective headwear 20 and the headgear 36.

In one example, by locating the pivots 98 of the occipital straps 80 above and forward of a wearer's ears in conjunction with the forehead strap 68 capable of pivoting about pivots 105, compressive force or pressure is directed to the forehead strap 68, which alleviates or decreases a constricting feeling, oftentimes experienced in conventional headgear, since the pressure or force is directed at major bone structures in a wearer's head and avoids applying compressing forces or pressures to areas of the wearer's head that are more likely to perceive pressure (e.g., soft tissue, concentration of nerves, etc.).

It should be understood that the headgear 36 may have a variety of shapes, sizes, and configurations and all of such possibilities are intended to be within the spirit and scope of the present disclosure.

It should be understood that the use of any orientation or directional terms herein such as, for example, "top", "bottom", "front", "rear", "back", "left", "right", "side", etc., is not intended to imply only a single orientation of the item with which it is associated or to limit the present disclosure in any manner. The use of such orientation or directional terms is intended to assist with the understanding of principles disclosed herein and to correspond to the exemplary orientation illustrated in the drawings. For example, the protective headwear 20 and headgear 36 may be utilized in any orientation and use of such terms is intended to correspond to the exemplary orientation of the protective headwear 20 and headgear 36 illustrated in the drawings. The use of these terms in association with the protective headwear 20 and headgear 36 is not intended to limit the protective headwear 20 and headgear 36 to a single orientation or to limit the protective headwear 20 and headgear 36 in any manner.

The Abstract of the disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

While various embodiments of the disclosure have been described, it will be apparent to those of ordinary skill in the art that other embodiments and implementations are possible within the scope of the disclosure. Accordingly, the disclosure is not to be restricted except in light of the attached claims and their equivalents.

The invention claimed is:

1. A headgear for engaging and supporting a protective shell on a wearer's head, the protective shell being rotatable relative to the headgear about a shell axis, the headgear comprising:
   a first side member positioned on a first side of the headgear, wherein the first side member includes a front end, a rear end opposite the front end and a first coupling location;
   a second side member positioned on a second side of the headgear opposite the first side, wherein the second side member includes a front end, a rear end opposite the front end and a second coupling location;
   a forehead strap pivotally coupled to the first and second side members, extending between the front ends of the first and second side members, and positioned on a front side of the shell axis, wherein the forehead strap pivots relative to one of the first and second side members about a pivot axis, and wherein the pivot axis is positioned on the front side of the shell axis;
   a top strap extending between the first and second side members and including a first end and a second end, wherein the first end of the top strap is directly coupled to the first side member at the first coupling location and the second end of the top strap is directly coupled to the second side member at the second coupling location; and an occipital strap having an end directly coupled to one of the first side member and the second side member in between a respective one of either the first or second coupling location and the front end of the one of the first side member and the second side member and on the front side of the shell axis, wherein the occipital strap extends above the shell axis and to a rear side of the shell axis opposite the front side.

2. The headgear of claim 1, wherein the occipital strap includes a body having an arcuate shape along at least a portion of the body.

3. The headgear of claim 1, wherein the occipital strap includes a body having a complex shape comprised of at least one linear portion and at least one arcuate portion.

4. The headgear of claim 3, wherein the body of the occipital strap has a first linear portion, a first arcuate portion, a second linear portion and a second arcuate portion.

5. The headgear of claim 1, wherein the occipital strap is pivotally coupled to the one of the first and second side members at the end of the occipital strap.

6. The headgear of claim 5, wherein the occipital strap and the forehead strap are pivotally coupled to the one of the first and second side members at a same location.

7. The headgear of claim 5, wherein the forehead strap and the occipital strap pivot about the pivot axis.

8. The headgear of claim 7, wherein the pivot axis is positioned above the shell axis.

9. The headgear of claim 1, further comprising a tightening member, wherein the occipital strap is engaged by the tightening member on the rear side of the headgear.

10. The headgear of claim 1, wherein the top strap is pivotally coupled to the first and second side members at the first and second coupling locations.

11. The headgear of claim 1, further comprising a rear strap coupled to and extending between the first and second side members.

12. The headgear of claim 11, wherein the rear strap is coupled to and extends between rear ends of the first and second side members.

13. The headgear of claim 11, wherein the rear strap is pivotally coupled to the first and second side members.

14. The headgear of claim 1, further comprising a pad coupled to the occipital strap.

15. A protective headwear comprising:
a shell;
a shield coupled to the shell and configured to allow at least partial viewing there through by a wearer of the protective headwear; and
a headgear pivotally coupled to the shell, wherein the headgear is configured to engage a wearer's head to support the shell relative to the wearer's head and facilitate pivoting of the shell about a shell axis relative to the headgear between a downward position and an upward position, wherein the headgear includes
a first side member on a first side of the headgear, wherein the first side member includes a front end, a rear end and a first coupling location,
a second side member on a second side of the headgear opposite the first side, wherein the second side member includes a front end, a rear end and a second coupling location,
a forehead strap coupled to and extending between the first and second side members on a front side of the shell axis, wherein the forehead strap is configured to engage a wearer's forehead with the headgear worn by a wearer,
a top strap including a first end and a second end and extending between the first side member and the second side member, wherein the first end of the top strap is directly coupled to the first side member at the first coupling location and the second end of the top strap is directly coupled to the second side member at the second coupling location, and
an occipital strap having a first end and a second end, wherein the first end is pivotally coupled to the first side member in between the first coupling location and the front end of the first side member and on the front side of and above the shell axis, wherein the occipital strap begins at the first end of the occipital strap, extends from the first end of the occipital strap, above the shell axis, and to a rear side of the shell axis opposite the front side where the occipital strap ends at the second end of the occipital strap, wherein the second end of the occipital strap is positioned on the rear side and below the shell axis, wherein the occipital strap pivots relative to the first side member about a pivot axis, and wherein the pivot axis is on the front side of and above the shell axis.

16. The protective headwear of claim 15, wherein the forehead strap is pivotally coupled to the first and second side members, and wherein the occipital strap and the forehead strap are pivotally coupled to the first side member at a same location.

17. The protective headwear of claim 15, wherein the forehead strap is pivotally coupled to the first and second side members, and wherein the forehead strap and the occipital strap pivot relative to the first side member about the pivot axis.

18. The protective headwear of claim 15, wherein the headgear further includes a tightening member, wherein the occipital strap is engaged by the tightening member on the rear side of the headgear.

19. The protective headwear of claim 15, wherein the protective headwear is a welding helmet and the shield is a welding shield.

20. The protective headwear of claim 15, wherein the occipital strap includes a body having an arcuate shape along at least a portion of the body.

21. The protective headwear of claim 15, wherein the occipital strap includes a body having a complex shape comprised of at least one linear portion and at least one arcuate portion.

22. The headgear of claim 21, wherein the body of the occipital strap has a first linear portion, a first arcuate portion, a second linear portion and a second arcuate portion.

23. A headgear for engaging and supporting a protective shell on a wearer's head, the headgear comprising:
a first side member positioned on a first side of the headgear, wherein the first side member includes a front end, a rear end opposite the front end and a first coupling location;
a second side member positioned on a second side of the headgear opposite the first side, wherein the second side member includes a front end, a rear end and a second coupling location;
a forehead strap pivotally coupled to the first and second side members and extending between the front ends of the first and second side members, wherein the forehead strap pivots relative to the first side member about a forehead pivot axis;
a top strap including a first end and a second end and extending between and engaging the first and second side members, wherein the first end of the top strap engages and directly couples to the first side member at the first coupling location and the second end of the top strap engages and directly couples to the second side member at the second coupling location, wherein the forehead pivot axis is positioned between the front end of the first side member and the first coupling location; and an occipital strap having an end coupled to the first side member in between the first coupling location and the front end of the first side member.

24. The headgear of claim 23, wherein the occipital strap is pivotally coupled to the first side member.

25. The headgear of claim 23, wherein the top strap is pivotally coupled to the first and second side members at the first and second coupling locations.

26. The headgear of claim 23, further comprising a rear strap coupled to and extending between the first and second side members.

27. The headgear of claim 26, wherein the rear strap is coupled to and extends between the rear ends of the first and second side members.

28. The headgear of claim 26, wherein the rear strap is pivotally coupled to the first and second side members.

29. The headgear of claim 23, wherein the occipital strap includes a pad configured to engage a wearer's head with the headgear supported on a wearers head.

* * * * *